United States Patent

Karrer

[11] 4,419,512
[45] Dec. 6, 1983

[54] N-SUBSTITUTED POLYALKYLPIPERIDINE-4-SPIROOXAZOLONES

[75] Inventor: Friedrich Karrer, Zofingen, Switzerland

[73] Assignee: Ciba-Geigy Corporation, Ardsley, N.Y.

[21] Appl. No.: 430,647

[22] Filed: Sep. 30, 1982

[30] Foreign Application Priority Data

Oct. 15, 1981 [CH] Switzerland ................... 6600/81

[51] Int. Cl.³ ................ C07D 498/10; C07D 498/20
[52] U.S. Cl. ......................... 544/70; 544/230; 546/19; 524/102
[58] Field of Search ............ 546/19; 544/70, 230; 524/102

[56] References Cited

U.S. PATENT DOCUMENTS

| | | | |
|---|---|---|---|
| 4,110,334 | 8/1978 | Mayer et al. | 546/19 |
| 4,220,773 | 9/1980 | Wiener et al. | 546/19 |
| 4,241,208 | 12/1980 | Murayama et al. | 546/20 |
| 4,263,505 | 4/1981 | Slongo et al. | 260/45.8 |

FOREIGN PATENT DOCUMENTS

| | | | |
|---|---|---|---|
| 2063573 | 7/1972 | Fed. Rep. of Germany | 546/19 |
| 2933732 | 3/1981 | Fed. Rep. of Germany | 546/19 |

Primary Examiner—Robert T. Bond
Attorney, Agent, or Firm—Harry Falber

[57] ABSTRACT

Compounds of the formulae Ia and Ib

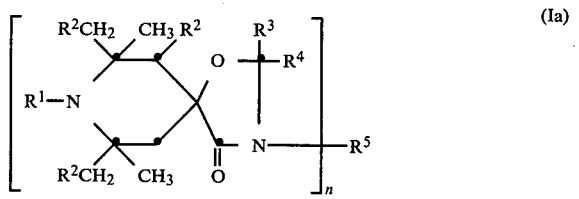

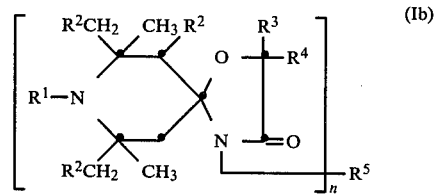

wherein n is 1 or 2, $R^1$ is an aliphatic or aromatic acyl radical, carbamoyl radical or —$CH_2CN$, and $R^2$, $R^3$, $R^4$ and $R^5$ are as defined in claim 1, have a much lower basicity than corresponding known compounds, in which $R^1$ is hydrogen or a hydrocarbon radical, but have at least as good a light stabilizing action as the known compounds. This is a substantial advantage for specific substrates.

3 Claims, No Drawings

N-SUBSTITUTED POLYALKYLPIPERIDINE-4-SPIROOXAZOLONES

The invention relates to novel polyalkylpiperidine-4-spirooxazolones and to their use as stabilisers for organic polymers, in particular against the action of light, as well as to the so stabilised polymers.

In German Offenlegungsschrift specifications 26 06 026, 28 34 962 and 29 33 732, and in European patent application 17 617, there have already been disclosed polyalkylpiperidine-4-spirooxazolones of the formulae A and B

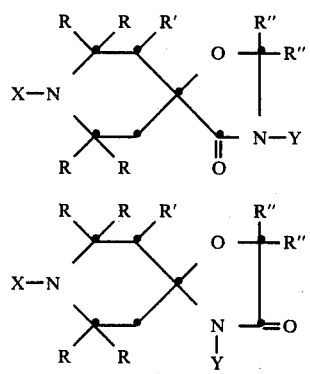

as light stabilisers for organic polymers, wherein R is alkyl, R' is hydrogen or alkyl, R'' is a monovalent hydrocarbon radical, X is hydrogen, oxygen, OH or an unsubstituted or substituted hydrocarbon radical, and Y is hydrogen or a hydrocarbon radical. All these compounds have a basic nitrogen atom in the piperidine ring and are therefore basic compounds which can form salts with acids. For specific fields of use the basicity of these compounds can be a drawback, for example for acid catalysed lacquers or for electrostatically or electrophoretically applied lacquers. There was accordingly a need for non-basic polyalkylpiperidine-4-spirooxazolones for such special fields of use.

It has been found that those compounds of the formulae A and B are suitable for such use in which X is an acyl, carbamoyl or cyanomethyl group. Accordingly, the invention provides compounds of the formula Ia or Ib

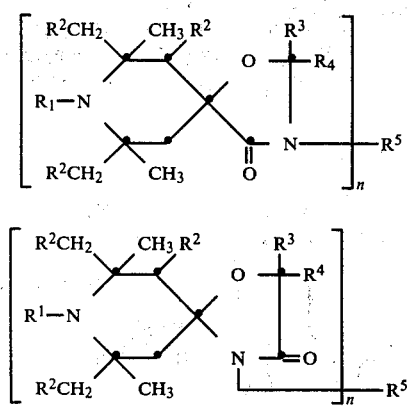

wherein n is 1 or 2;

$R^1$ is $C_2-C_{30}$alkanoyl, $C_3-C_{20}$alkenoyl, —$CH_2CN$, —CO—$N(R^6)(R^7)$, $C_7-C_{11}$aroyl, $C_8-C_{14}$arylalkanoyl or $C_8-C_{20}$alkylaroyl;

$R^2$ is hydrogen or $C_1-C_4$alkyl; each of $R^3$ and $R^4$ independently of the other is hydrogen, $C_1-C_{30}$alkyl, unsubstituted or chlorine- or alkyl-substituted $C_6-C_{10}$aryl, unsubstituted or alkyl-substituted $C_7-C_{11}$aralkyl, or $R^3$ and $R^4$, together with the carbon atom to which they are attached, form a cycloalkane or alkylcycloalkane ring containing 5 to 18 carbon atoms, or a group of the formula

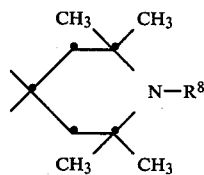

$R^5$, when n is 1, is $C_1-C_{30}$alkyl, $C_3-C_{20}$alkenyl, unsubstituted or alkyl-substituted $C_7-C_{11}$aralkyl, or is $C_5-C_{12}$cycloalkyl, $C_2-C_{18}$alkanoyl, $C_3-C_{18}$alkenoyl, $C_7-C_{11}$aroyl, $C_8-C_{14}$arylalkanoyl or $C_8-C_{20}$alkylaroyl, or $R^5$, when n is 2, is $C_2-C_{30}$alkylene, $C_2-C_{30}$alkenylene or $C_8-C_{18}$arylenedialkylene;

$R^6$ is hydrogen, $C_1-C_{18}$alkyl, $C_5-C_8$cycloalkyl, $C_7-C_{15}$aralkyl or $C_6-C_{10}$aryl;

$R^7$ is $C_1-C_{18}$alkyl, $C_5-C_8$cycloalkyl, $C_7-C_{15}$aralkyl or $C_6-C_{10}$aryl; or $R^6$ and $R^7$, together with the nitrogen atom, form a 5- to 7-membered ring which can be interrupted by further hetero-atoms; and $R^8$ is hydrogen, $C_1-C_{12}$alkyl, $C_3-C_5$alkenyl, $C_3-C_5$alkynyl, unsubstituted or alkyl-substituted $C_7-C_{11}$aralkyl, $C_2-C_{18}$alkanoyl, $C_3-C_{18}$alkenoyl, —$CH_2CN$ or —CO—$N(R^6)(R^7)$.

$R^2$, $R^3$, $R^4$, $R^5$, $R^6$, $R^7$ and $R^8$ can be unbranched or branched alkyl. Within the scope of the defined number of carbon atoms, examples of such alkyl groups are methyl, ethyl, isopropyl, sec-butyl, tert-butyl, hexyl, octyl, dodecyl, tetradecyl, heptadecyl, octadecyl, eicosyl, docosyl or triacontyl.

Within the scope of the defined number of carbon atoms, $R^5$ and $R^8$ as alkenyl can be e.g. allyl, methallyl, 3,3-dimethylallyl, 1-buten-4-yl, 2-hepten-1-yl or oleyl. $R^8$ is alkenyl can be e.g. propargyl, butynyl or pentynyl.

$R^5$, $R^6$ and $R^7$ as cycloalkyl can be e.g. cyclopentyl, cyclohexyl or cyclooctyl. $R^5$ can also be e.g. methylcyclohexyl, dimethylcyclopentyl or cyclododecyl.

$R^3$, $R^4$, $R^6$ and $R^7$ as aryl can be phenyl or naphthyl, and $R^3$ and $R^4$ can also be e.g. chloroaryl or alkyl-substituted aryl, in particular phenyl substituted by $C_1-C_4$alkyl. Examples of such groups are chlorophenyl, chloronaphthyl, mono- or dimethylphenyl, nonylphenyl or dodecylphenyl.

$R^3$, $R^4$, $R^5$, $R^6$, $R^7$ and $R^8$ as aralkyl can be e.g. phenylethyl, phenylisopropyl and, in particular, benzyl. Examples of $R^3$, $R^4$, $R^5$ and $R^8$ as alkylated aralkyl are methylnaphthylmethyl, octylbenzyl, nonylbenzyl, dodecylbenzyl and, in particular, benzyl substituted by $C_1-C_4$alkyl, e.g. methylbenzyl, isopropylbenzyl or tert-butylbenzyl.

A cycloalkane ring formed by $R^3$ and $R^4$ together with the carbon atom to which they are attached can be e.g. a cyclohexane, cyclooctane or cyclododecane ring.

A 5- to 7-membered ring formed by $R^6$ and $R^7$, together with the nitrogen atom to which they are attached, can be e.g. a pyrrolidine, piperidine, morpholine or piperazine ring.

$R^5$ as alkylene can be unbranched or branched alkylene, e.g. ethylene, hexamethylene, octamethylene, dodecylmethylene, 1,2-propylene or 2,2-dimethylpropylene-1,3. $R^5$ as alkylene can be e.g. 2-butylene-1,4 or 2,3-dimethyl-2-butenylene-1,4. $R^5$ as arylene-dialkylene can be e.g. phenylenediethylene or naphthylenedimethylene, and, in particular m- or p-xylylene.

$R^1$, $R^5$ and $R^8$ as aliphatic acyl radicals can be e.g. acetyl, propionyl, butyryl, hexanoyl, octanoyl, dodecanoyl or octadecanoyl (stearoyl). $R^1$ can also be e.g. eicosanoyl, docosanoyl, tricontanoyl, acryloyl, methacryloyl, crotonoyl, hexenoyl or octadecenoyl (oleoyl).

$R^1$ and $R^5$ as aromatic acyl radicals can be e.g. benzoyl, naphthoyl, phenylacetyl, phenylpropionyl, naphthylacetyl, toluyl, dimethylbenzoyl, 4-butylbenzoyl, 4-octylbenzoyl or 4-dodecylbenzoyl.

Preferred compounds of the formula YIa Yor Ib are those wherein $R^1$ is $C_2$-$C_{12}$alkanoyl, $C_3$-$C_5$alkenoyl, phenylacetyl, —$CH_2CN$ or —CO—N($R^6$)($R^7$);
$R^2$ is hydrogen;
each of $R^3$ and $R^4$ independently of the other is hydrogen, $C_1$-$C_{12}$alkyl, $C_7$-$C_{12}$aralkyl or phenyl substituted by $C_1$-$C_4$alkyl, or $R^3$ and $R^4$, together with the carbon atom to which they are attached, form a cycloalkane or alkylcycloalkane ring containing 5 to 12 carbon atoms or a group of the formula

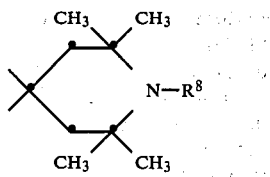

$R^5$, when n is 1, is $C_1$-$C_{18}$alkyl, $C_3$-$C_6$alkenyl, $C_5$-$C_6$cycloalkyl, $C_7$-$C_{12}$aralkyl, $C_2$-$C_{12}$alkanoyl or $C_3$-$C_{12}$alkenoyl, and when n is 2, is $C_2$-$C_{18}$alkylene, $C_4$-$C_{12}$alkenylene or xylylene;
$R^6$ is hydrogen, $C_1$-$C_{12}$alkyl, $C_5$-$C_6$cycloalkyl, $C_7$-$C_{12}$aralkyl or phenyl;
$R^7$ is $C_1$-$C_{12}$alkyl, $C_5$-$C_6$cycloalkyl, $C_7$-$C_{12}$aralkyl or $C_6$-$C_{10}$aryl, or $R^6$ and $R^7$, together with the nitrogen atom to which they are attached, form a 5- to 7-membered ring; and $R^8$ is hydrogen, $C_1$-$C_6$alkyl, $C_3$-$C_5$alkenyl, benzyl, $C_2$-$C_{12}$alkanoyl, $C_3$-$C_{12}$alkenoyl, propargyl or cyanomethyl.

Particularly preferred are compounds of the formula Ia, wherein n is 1; $R^1$ is $C_2$-$C_{12}$alkanoyl, $C_3$-$C_5$alkenoyl, —CO—N($R^6$)($R^7$) or —$CH_2CN$; $R^2$ is hydrogen; each of $R^3$ and $R^4$ independently of the other is hydrogen, $C_1$-$C_4$alkyl, benzyl or phenyl, or $R^3$ and $R^4$, together with the carbon atom to which they are attached, form a $C_5$-$C_{12}$cycloalkane ring; $R^5$ is $C_1$-$C_6$alkyl, $C_3$-$C_5$alkenyl, benzyl, $C_2$-$C_{12}$alkanoyl or $C_3$-$C_5$alkenoyl; $R^6$ is hydrogen, $C_1$-$C_6$alkyl, cyclohexyl, benzyl or phenyl; and $R^7$ is $C_1$-$C_6$alkyl, cyclohexyl, benzyl or phenyl; or $R^6$ and $R^7$, together with the nitrogen atom to which they are attached, form a 5- to 7-membered ring.

Examples of compounds of the formula Ia, wherein n is 1, are:

8-acetyl-2,2,7,7,9,9-hexamethyl-1-oxa-3,8-diaza-4-oxo-spiro[4.5]decane,
8-acryloyl-2,2,7,7,9,9-hexamethyl-1-oxa-3,8-diaza-4-oxo-spiro[4.5]-decane,
3-methacryloyl-2,2,4,4-tetramethyl-7-oxa-3,14-diaza-15-oxo-dispiro[5.1.5.2]pentadecane,
3-acryloyl-2,2,4,4-tetramethyl-20-allyl-7-oxa-3,20-diaza-21-oxo-dispiro[5.1.11.2]heneicosane,
8-acryloyl-2,2,7,7,9,9-hexamethyl-3-benzyl-1-oxa-3,8-diaza-4-oxo-spiro[4,5]decane,
8-acryloyl-7,7,9,9-tetramethyl-3-octadecyl-2,2-diethyl-1-oxa-3,8-diaza-4-oxo-spiro[4,5]decane,
3-acetyl-2,2,4,4-tetramethyl-20-allyl-7-oxa-3,20-diaza-21-oxo-dispiro[5.1.11.2]heneicosane,
3-acryloyl-2,2,4,4-tetramethyl-20-benzyl-7-oxo-3,20-diaza-21-oxo-dispiro[5.1.11.2]heneicosane,
3,20-diheptadecanoyl-2,2,4,4-tetramethyl-7-oxa-3,20-diaza-21-oxo-dispiro[5.1.11.2]heneicosane,
3-acetyl-2,2,4,4-tetramethyl-20-benzyl-7-oxa-3,20-diaza-21-oxo-dispiro[5.1.11.2]heneicosane,
3-(N,N-diethyl)-carbamoyl-2,2,4,4-tetramethyl-7-oxa-3,20-diaza-21-oxo-dispiro[5.1.11.2]heneicosane,
3-(N,N-dioctyl)-carbamoyl-2,2,4,4-tetramethyl-20-octadecyl-7-oxa-3,20-diaza-21-oxo-dispiro[5.1.11.2]heneicosane,
3-phenylcarbamoyl-2,2,4,4-tetramethyl-20-octadecyl-7-oxa-3,20-diaza-21-oxo-dispiro[5.1.11.2]heneicosane,
8-cyclohexylcarbamoyl-2,2,7,7,9,9-hexamethyl-3-hexyl-1-oxa-3,8-diaza-4-oxo-spiro[4,5]decane.

Examples of compounds of the formula Ia, wherein n is 2, are:

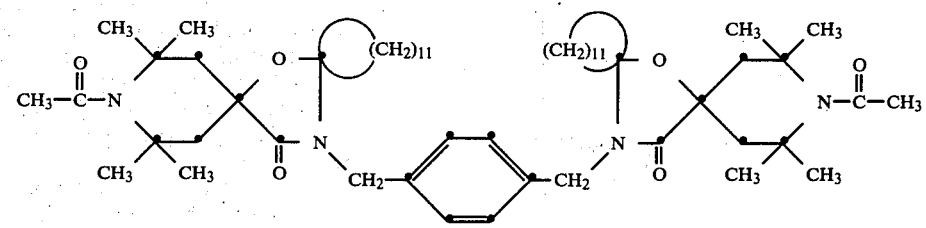

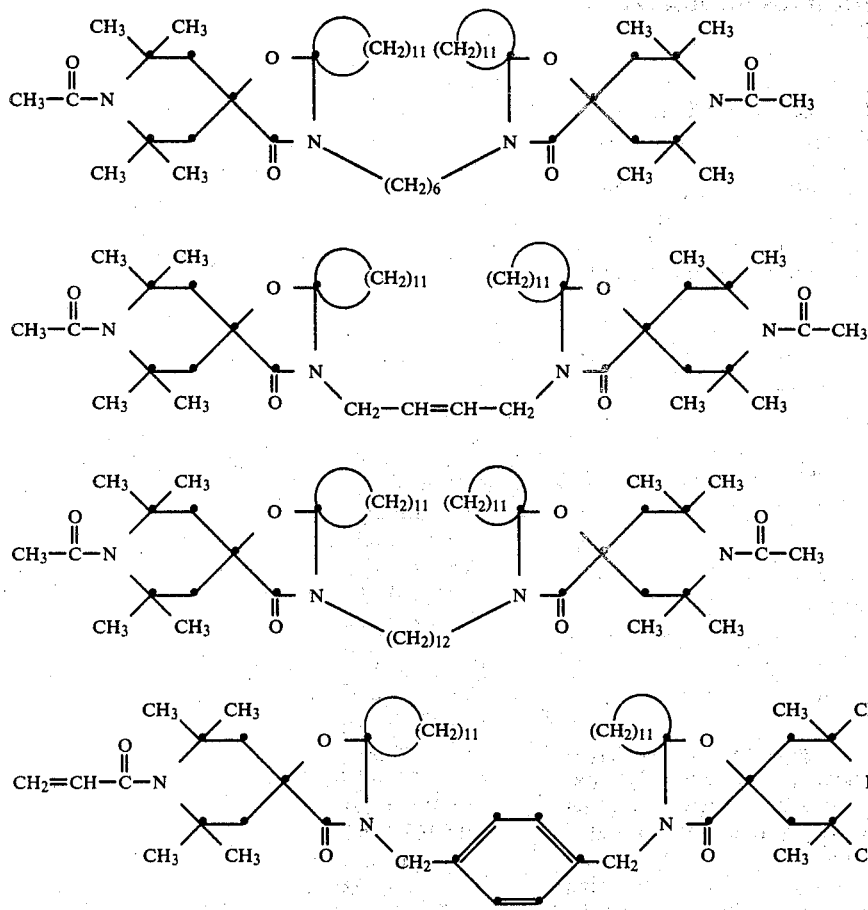

Examples of compounds of the formula Ib, wherein n is 1, are:
8-acetyl-2,2,4,7,7,9,9-heptamethyl-1-oxa-4,8-diaza-3-oxo-spiro[4.5]decane,
8-acetyl-2,2,7,7,9,9-hexamethyl-1-oxa-4,8-diaza-3-oxo-spiro[4.5]decane,
8-acetyl-7,7,9,9-tetramethyl-2-cyclohexyl-4-allyl-1-oxa-4,8-diaza-3-oxo-spiro[4.5]decane,
8-benzylcarbonyl-7,7,9,9-tetramethyl-2,2-dibenzyl-1-oxa-4,8-diaza-3-oxo-spiro[4.5]decane,
8-decanoyl-2,2,7,7,9,9-hexamethyl-1-oxa-4,8-diaza-3-oxo-spiro[b 4.5]decane,
8-methacryloyl-2,2,4,7,7,9,9-heptamethyl-1-oxa-4,8-diaza-3-oxo-spiro[4.5]decane,
8-acetyl-2,2,7,7,9,9-hexamethyl-4-benzyl-1-oxa-4,8-diaza-3-oxo-spiro[4.5]decane,
8-acryloyl-2,2,7,7,9,9-hexamethyl-1-oxa-4,8-diaza-3oxo-spiro[4.5]decane,
8-[N,N-dibutyl]-carbamoyl-2,2,7,7,9,9-hexamethyl-1-oxa-4,8-diaza-3-oxo-spiro[4.5]decane,
4,8-bisacryloyl-2,2,7,7,9,9-hexamethyl-1-oxa-4,8-diaza-3-oxo-spiro[4.5]decane,
3-acetyl-2,2,4,4-tetramethyl-7-oxa-3,21-diaza-20-oxo-dispiro[5.1.11.2]heneicosane,
3,21-diacetyl-2,2,4,4-tetramethyl-7-oxa-3,21-diaza-20-oxo-dispiro[5.1.11.2]heneicosane,
3-acryloyl-2,2,4,4-tetramethyl-7oxa-3,21-diaza-20-oxo-dispiro[5.1.11.2]heneicosane,
3-[N,N-diethyl]-carbamoyl-2,2,4,4-tetramethyl-7-oxa-3,21-diaza-20-oxo-dispiro[5.1.11.2]heneicosane.

Examples of compounds of the formula Ib, wherein n is 2, are:

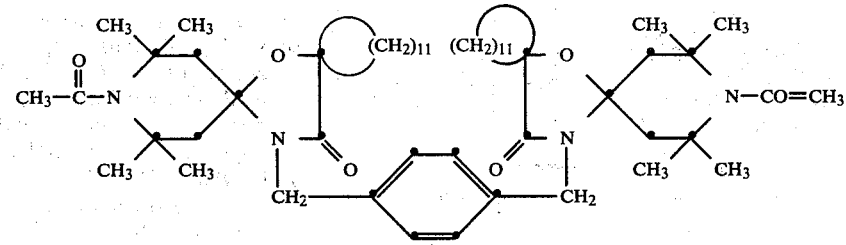

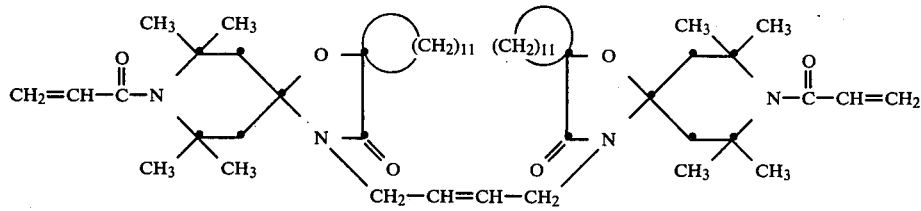

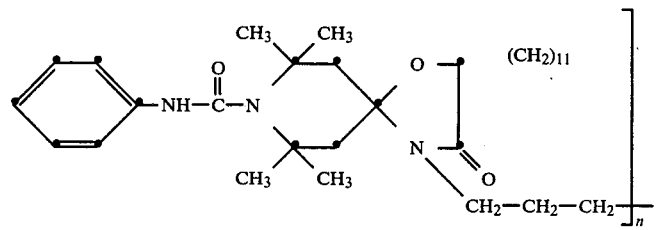

The compounds of the formula Ia can be prepared from the corresponding compounds of the formula IIa

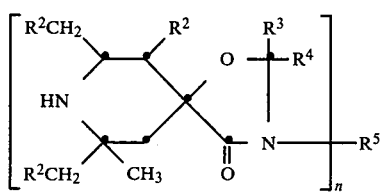

by substitution at the piperidine-nitrogen. Suitable methods are those generally employed for the N-acylation of secondary amines. Alkanoyl, alkenoyl, aroyl, arylalkanoyl and alkylaroyl radicals can be introduced by reaction with the corresponding carboxylic acid chlorides $R^1Cl$, in the presence of a proton acceptor, or with the carboxylic acid anhydrides $(R^1)_2O$. A carbamoyl radical $-CO-N(R^6)(R^7)$ can be introduced by the stepwise reaction of IIa with (a) phosgene and (b) an amine $R_7{}^6-NH-R^7$, or by reaction with a carbamoyl chloride $(R^6)(R^7)N-CO-Cl$. Carbamoyl radicals, in which $R^6$ is hydrogen, are obtained from IIa by reaction with an isocyanate $R^7-NCO$.

If a start is made from a compound IIa in which $R^5$ is hydrogen, then both nitrogen atoms can also be substituted simultaneously in these acylation reactions to give compounds of the formula Ia, wherein $R^5$ has the same meaning as $R^1$.

The introduction of a cyanomethyl radical as $R^1$ can be effected by reaction of IIa with formaldehyde and hydrogen cyanide or formaldehyde and an alkali cyanide.

The compounds of the formula Ib can be prepared in analogous manner from the compounds of the formula IIb

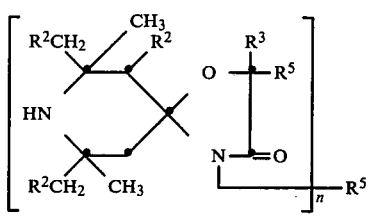

by substitution at the piperidine-nitrogen.

Compounds of the formulae IIa and IIb are known compounds. Their preparation is described e.g. in German Offenlegungsschrift specifications 26 06 026, 28 34 962 and 29 33 732, or can be effected in analogous manner.

The compounds of formulae Ia and Ib are suitable as stabilisers for organic polymers against the action of light, heat and oxygen and have, in particular, an outstanding light stabilising action.

Examples of such polymers are:

1. Polymers of mono- and diolefins, for example polyethylene (which can be crosslinked), polypropylene, polyisobutylene, polybut-1-ene, polymethylpent-1-ene, polyisoprene or polybutadiene, and polymers of cyclo-olefins, e.g. of cyclopentene or norbornene.

2. Mixtures of the polymers mentioned under (1), for example mixtures of polypropylene with polyethylene or with polyisobutylene.

3. Copolymers of mono- and diolefins with each other or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkylacrylate copolymers, ethylene/alkylmethacrylate copolymers, ethylene/vinyl acetate copolymers, or ethylene/acrylic acid copolymers and salts thereof (ionomers), and also terpolymers of ethylene with propylene and a diene, such as hexadiene, dicyclopentadiene or ethylidenenorbornene.

4. Polystyrene.

5. Copolymers of styrene or α-methylstyrene with dienes or acrylic derivatives, for example styrene/butadiene, styrene/acrylonitrile, styrene/alkylmethacrylate, styrene/acrylonitrile/methyl acrylate; mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene, or styrene-ethylene/propylene-styrene.

6. Graft copolymers of styrene, e.g. styrene with polybutadiene, styrene and acrylonitrile with polybutadiene, styrene and maleic anhydride with polybutadiene, styrene and alkyl acrylates or alkyl methacrylates with polybutadiene, styrene and acrylonitrile with ethylene-propylene-diene terpolymers, styrene and acrylonitrile with polyalkylacrylates or polyalkylmethacrylates, styrene and acrylonitrile with acrylate-butadiene copolymers, and mixtures thereof with the copolymers listed under (5), known e.g. as ABS, MBS, ASA or AES polymers.

7. Halogen-containing polymers, e.g. polychloroprene, chlorinated rubber, chlorinated or chlorosulfonated polyethylene, especially polymers of halogenated vinyl compounds, e.g. polyvinyl chloride, polyvinylidene chloride, polyvinyl fluoride, polyvinylidene fluoride, and their copolymers such as vinyl chloride/vinylidene chloride, vinyl chloride/vinyl acetate or vinylidene chloride/vinyl acetate.

8. Polymers which are derived from $\alpha,\beta$-unsaturated acids and their derivatives, such as polyacrylates and polymethacrylates, polyacrylamides and polyacrylonitriles.

9. Copolymers of the monomers listed in (8) with one another or with other unsaturated monomers, e.g. acrylonitrile/butadiene copolymers, acrylonitrile/alkyl acrylate copolymers, acrylonitrile/vinyl chloride copolymers, or acrylonitrile/alkyl methacrylate/butadiene terpolymers.

10. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinylbutyral, polyallyl phthalate, polyallylmelamine.

11. Homopolymers and copolymers of cyclic ethers such as polyethylene glycols, polyethylene oxide, polypropylene oxide or their copolymers with bis-glycidyl ethers.

12. Polyacetals such as polyoxymethylene, and also those polyoxymethylenes which contain a comonomer, e.g. ethylene oxide.

13. Polyphenylene oxides and sulfides.

14. Polyurethanes which are derived on the one hand from polyethers, polyesters and polybutadienes containing hydroxyl end groups, and from aliphatic or aromatic polyisocyanates on the other, as well as their precursors (polyisocyanates, polyols, prepolymers).

15. Polyamides and copolyamides which are derived from diamines and dicarboxylic acids and/or from aminocarboxylic acids or the corresponding lactams, such as polyamide 4, polyamide 6, polyamide 66, polyamide 610, polyamide 11, polyamide 12, poly-2,4,4-trimethylhexamethyleneterephthalamide, poly-m-phenylene-isophthalamide, and their copolymers with polyethers, e.g. with polyethylene glycol, polypropylene glycol or polytetramethylene glycol.

16. Polyureas, polyamides and polyamide imides.

17. Polyesters which are derived from dicarboxylic acids and dialcohols and/or from hydroxycarboxylic acids or the corresponding lactones, such as polyethylene terephthalate, polybutylene terephthalate and poly-1,4-dimethylolcyclohexane terephthalate, poly-[2,2-bis(4-hydroxyphenyl)propane]-terephthalate, polyhydroxybenzoates, and also block polyether esters which are derived from polyethers having hydroxyl end groups, dialcohols and dicarboxylic acids.

18. Polycarbonates.

19. Polysulfones and polyether sulfones.

20. Crosslinked polymers which are derived from aldehydes on the one hand and from phenols, ureas and melamines on the other hand, such as phenol-formaldehyde resins, urea-formaldehyde resins and melamine-formaldehyde resins.

21. Drying and non-drying alkyd resins.

22. Unsaturated polyester resins which are derived from copolyesters of saturated and unsaturated dicarboxylic acids with polyhydric aclcohols and vinyl compounds as crosslinking agents, and also their halogen-containing flame-resistant modifications.

23. Crosslinkable acrylic resins which are derived from substituted acrylic esters, e.g. from epoxy acrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, e.g. bis-glycidyl ethers, or from cycloaliphatic diepoxides.

26. Naturally occurring polymers, such as cellulose, natural rubber and gelatin, and also the chemically modified homologous derivatives thereof, such as cellulose acetates, cellulose propionates and cellulose butyrates, and cellulose ethers such as methylcellulose.

Of particular importance is the stabilising of lacquers such as alkyd, acrylic and polyester lacquers, in particular the stabilising of acid catalysed stoving lacquers.

The stabilisers of this invention are incorporated in the polymers in a concentration of 0.01 to 5% by weight, based on the material to be stabilised. Preferably 0.1 to 2% by weight of the compounds, based on the material to be stabilised, is incorporated thereinto.

Incorporation can be effected after polymerisation, for example by blending the compounds and, if desired, further additives, into the melt by methods conventionally employed in the art, before or during the manufacture of shaped articles therefrom, or also by applying the dissolved or dispersed compounds to the polymer, with or without subsequent evaporation of the solvent.

The stabilisers can also be added in the form of a master batch which contains these compounds, for example in a concentration of 2.5 to 25% by weight, to the polymers to be stabilised.

In addition to the compounds of the formulae Ia and Ib, still further known stabilisers can also be incorporated in the polymers. These stabilisers can be e.g. antioxidants, light stabilisers or metal deactivators, or also costabilisers, for example thos of the phosphite type. Furthermore, other additives customary in plastics technology, for example flame retardants, antistatic agents, plasticisers, lubricants, blowing agents, pigments, reinforcing materials or fillers, can also be added.

When known stabilisers are used concurrently, synergistic effects can be obtained. This frequently happens especially when other light stabilisers or organic phosphites are used concurrently. The concurrent use of antioxidants when stabilising polyolefins is of particular importance.

The invention thereof also relates to the plastics stabilised by the addition of 0.1 to 5% by weight of a compound of the formula I, which plastics, if desired, can also contain other known and customary additives. The stabilised plastics can be used in very diverse forms, for example as films, fibres, ribbons or profiles, but especially as binders for lacquers.

The manufacture and use of the compounds of the invention is described in more detail in the following Examples. Parts and percentages are by weight.

EXAMPLE 1

51 g (0.14 mole) of 2,2,4,4-tetramethyl-7-oxa-3,20-diaza-21-oxo-dispiro[5.1.11.2]heneicosane in 400 ml of acetic anhydride and 4 ml of dimethyl formamide are heated for 22 hours to 110°-115° C. With stirring, the reaction mixture is then cooled to room temperature and filtered. The filtrate is worked up as described hereinbelow. The crystalline precipitate is recrystallised from dimethyl formamide, washed with water and then with acetone and vacuum dried, affording 3-acetyl-2,2,4,4-tetramethyl-7-oxa-3,20-diaza-21-oxo-dispiro[5.1.11.2]heneicosane of the formula

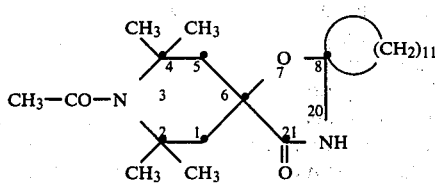

which melts at 234°-236° C. (stabiliser 1).

| Analysis C$_{24}$H$_{42}$N$_2$O$_3$ | calc.: | C 70.89 | H 10.41 | N 6.89% |
|---|---|---|---|---|
| (406.61) | found: | C 70.6 | H 10.5 | N 7.0% |

The acetic anhydride filtrate obtained above is evaporated to dryness in vacuo. The residue, which crystallises after a short time, is recrystallised twice from acetonitrile, affording pure 3,20-diacetyl-2,2,4,4-tetramethyl-7-oxa-3,20-diaza-21-oxo-dispiro[5.1.11.2]heneicosane of the formula

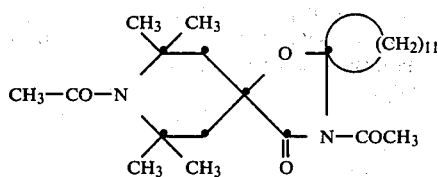

which melts at 183°-185° C.

| Analysis C$_{26}$H$_{44}$N$_2$O$_4$ | calc.: | C 69.60 | H 9.88 | N 6.24% |
|---|---|---|---|---|
| (448.65) | found: | 69.6 | 9.8 | 6.4% |

The mono- and diacetyl compounds can be readily identified by thin-layer chromatography and show the expected signals in the $^1$H-NMR spectrum.

EXAMPLE 2

27.3 g of 2,2,4-tetramethyl-20-benzyl-7-oxa-3,20-diaza-21-oxa-dispiro[5.1.11.2]heneicosane are dissolved in 130 ml of toluene. After addition of 5.4 g of paraformaldehyde the contents of the flask are heated to 85° C. Hydrocyanic acid is then introduced at this temperature over about 10 hours into the reaction mixture (a total of 8.2 g), which is subsequently stirred for 12 hours at 85° C. Then, still at the same temperature, nitrogen is passed through the yellow solution over 6 hours. The solvent is stripped off in vacuo and the residue is recrystallised from methyl ethyl ketone with the addition of activated carbon, yielding 3-cyanomethyl-2,2,4,4-tetramethyl-20-benzyl-7-oxa-3,20-diazo-21-oxo-dispiro[5.1.11.2]heneicosane which melts at 192°-192° C. (stabiliser 2).

| Analysis C$_{31}$H$_{47}$N$_3$O$_2$ | calc.: | C 75.41 | H 9.60 | N 8.51% |
|---|---|---|---|---|
| (493.7) | found: | 75.1 | 9.3 | 8.4% |

EXAMPLE 3

25 g (55 mmoles) of 2,2,4,4-tetramethyl-20-benzyl-7-oxa-3,20-diazo-21-oxo-dispiro[5.1.11.2]heneicosane, 9.5 ml of triethylamine and 100 mg of 2,6-di-tert-butyl-4-methylphenol are dissolved in 70 ml of chloroform and the solution is cooled to −20° C. A solution of 5.23 g (58 mmoles) of acryloyl chloride in 10 ml of chloroform is added dropwise at −10° to −12° C. over about 1 hour to the above solution. The reaction mixture is then stirred for 4 hours at −10° C. and the contents of the flask are diluted with 250 ml of hexane, clarified, and extracted with four 25 ml portions of water. The organic phase is dried over Na$_2$SO$_4$ and then concentrated in vacuo. Crystallisation of the residue from acetonitrile/methyl ethyl ketone yields 3-acryloyl-2,2,4,4-tetramethyl-20-benzyl-7-oxa-3,20-diaza-21-oxo-dispiro[5.1.11.2]heneicosane with a melting point of 174°-176° C. (stabiliser 3).

| Analysis C$_{32}$H$_{48}$N$_2$O$_3$ | calc.: | C 75.55 | H 9.51 | N 5.51% |
|---|---|---|---|---|
| (508.7) | found: | 75.4 | 9.3 | 5.5%. |

In corresponding manner, reaction of 2,2,4,4-tetramethyl-20-alkyl-7-oxa-3,20-diaza-21-oxo-dispiro[5.1.11.2]heneicosane and diethylcarbamoyl chloride gives 3-diethylcarbamoyl-2,2,4,4-tetramethyl-20-alkyl-7-oxa-3,20-diaza-21-oxo-dispiro[5.1.11.2]heneicosane with a melting point of 99°-101° C. (stabiliser 4).

| Analysis C$_{30}$H$_{53}$N$_3$O$_3$ | calc.: | C 71.53 | H 10.60 | N 8.34% |
|---|---|---|---|---|
| (503.8) | found: | 71.7 | 10.4 | 8.1%. |

EXAMPLE 4

13.6 g (30 mmoles) of 2,2,4,4-tetramethyl-20-benzyl-7-oxa-3,20-diaza-21-oxo-dispiro[5.1.11.2]heneicosane and 0.03 g of 1,4-diazabicyclo[2.2.2]octane (DABCO) are dissolved in 70 ml of benzene. A solution of 2.97 g (30 mmoles) of butyl isocyanate in 10 ml of benzene is added dropwise at room temperature over about 45 minutes to the above solution and the reaction is allowed to go completion for 24 hours at room temperature. The reaction mixture is concentrated to half of its volume and diluted with diethyl ether. The colourless precipitate is filtered with suction, washed with ethyl ether and dried, affording 3-butyl-carbamoyl-2,2,4,4-tetramethyl-20-benzyl-7-oxa-3,20-diaza-21-oxo-dispiro[5.1.11.2]heneicosane with a melting point of 148°-150° C. (stabiliser 5).

| Analysis C$_{34}$H$_{55}$N$_3$O$_3$ | calc.: | C 73.74 | H 10.01 | N 7.59% |
|---|---|---|---|---|
| (553.8) | found: | 73.3 | 10.0 | 7.9% |

The following compounds are obtained in the same manner from the corresponding starting materials:

3-cyclohexylcarbamoyl-2,2,4,4-tetramethyl-20-allyl-7-oxa-3,20-diaza-21-oxo-dispiro[5.1.11.2]heneicosane with a melting point of 140°–142° C. (stabiliser 6),
3-phenylcarbamoyl-2,2,4,4-tetramethyl-20-allyl-7-oxa-3,20-diaza-21-oxo-dispiro[5.1.11.2]heneicosane with a melting point of 124°–127° C. (stabiliser 7).

EXAMPLE 5

19.6 g of 2,2,4,4-tetramethyl-20-allyl-7-oxa-3,20-diaza-21-oxo-dispiro[5.1.11.2]heneicosane and 80 ml of acetic anhydride are stirred for 24 hours at 90°–95° C. Excess anhydride and the acetic acid formed are distilled off in vacuo as completely as possible. The crystalline residue is recrystallised from acetonitrile affording 3-acetyl-2,2,4,4-tetramethyl-20-allyl-7-oxa-3,20-diaza-21-oxo-dispiro[5.1.11.2]-heneicosane with a melting point of 113°–114° C. (stabiliser 8).

| Analysis $C_{27}H_{46}N_2O_3$ | calc.: | C 72.6 | H 10.38 | N 6.27% |
|---|---|---|---|---|
| (446.8) | found: | 72.5 | 10.2 | 6.4 |

The following compounds are obtained in similar manner from the corresponding starting materials:
3-acetyl-2,2,4,4-tetramethyl-20-benzyl-7-oxa-3,20-diaza-21-oxo-dispiro[5.1.11.2]heneicosane with a melting point of 128°–129° C. (stabiliser 9),
3-acetyl-2,2,4,4-tetramethyl-20-butylcarbamoyl-7-oxa-3,20-diaza-21-oxo-dispiro[5.1.11.2]heneicosane with a melting point of 176°–178° C. (stabiliser 10),
3-acetyl-2,2,4,4-tetramethyl-20-hexyl-7-oxa-3,20-diaza-21-oxo-dispiro[5.1.11.2]heneicosane with a melting point of 89°–91° C. (stabiliser 11),
1,4-bis(3-acetyl-2,2,4,4-tetramethyl-7-oxa-3,20-diaza-21-oxo-dispiro[5.1.11.2]heneicosyl-20)-but-2-ene with a melting point of 156°–158° C. (stabiliser 12).

EXAMPLE 6

A solution of 2.48 g of phosgene is stirred dropwise at 0° C. over 1 hour into a solution of 20.2 g of 2,2,4,4-tetramethyl-20-alkyl-7-oxa-3,20-diaza-21-oxo-dispiro[5.1.11.2]heneicosane in 120 ml of ethyl acetate. Stirring is continued for 16 hours at room temperature and then a solution of 1.5 g of ethanol and 2.5 g of triethylamine in 10 ml of ethyl acetate is added dropwise. After stirring for 8 hours the reaction mixture is filtered and the filtrate is washed twice with water, three times with ice-cold n-HCl and again with water, dried over $Na_2SO_4$ and concentrated in vacuo. The residual crude product is purified by chromatography over a silica gel column with a 3:2 mixture of diethyl ether/hexane as eluant, and recrystallised from pentane. The pure 3-ethoxycarbonyl-2,2,4,4-tetramethyl-20-alkyl-7-oxa-3,20-diaza-21-oxo-dispiro[5.1.11.2]heneicosane has a melting point of 81°–82° C. (stabiliser 13).

| Analysis $C_{28}H_{48}N_2O_4$ | calc.: | C 70.55 | H 10.15 | N 5.88% |
|---|---|---|---|---|
| (476.7) | found: | 70.8 | 10.0 | 6.0%. |

The $^1$H-NMR spectrum is in accord with the indicated structure.

EXAMPLE 7: Stabilisation of propylene against light 100 parts of polypropylene powder (Moplen, fibre grade, manufactured by Montedison), 0.2 part of β-(3,5-di-tert-butyl-4-hydroxyphenyl)-propionic acid octadecyl ester, 0.1 part of calcium stearate and 0.25 part of a stabiliser of Table 1 are homogenised in a Brabender plastograph for 10 minutes at 200° C. The resultant plastic mass is removed from the kneader as quickly as possible and pressed to a 2–3 mm sheet in a toggle press. A portion of the sheet is cut out and pressed between two ultra-gloss rigid aluminium sheets with a hand-operated hydraulic laboratory press for 6 minutes at 260° to a 0.1 mm sheet, which is immediately chilled in cold water. Segments are then punched out of this sheet and exposed in the xenotest 1200. These samples are taken out of the exposure apparatus at regular intervals and examined for their carbonyl content in a IR spectrophotometer. The increase in the carbonyl extinction at 5.85μ during exposure is a reference value for the degradation of the polymer by photooxidation [see L. Balaban et al., J. Polymer Sci., Part C; 22, 1059–1071 (1969)] and, as experience shows, is associated with a decrease in the mechanical properties of the polymer. The time taken till a carbonyl extinction of about 0.3 is reached, at which value the comparison sheet is brittle, serves as an indication of the protective action.

TABLE I

| Stabiliser | Exposure time in hours |
|---|---|
| 2 | >2100 |
| 3 | >2200 |
| 4 | >2200 |
| 5 | >1600 |
| 6 | >2200 |
| 7 | >1700 |
| 8 | >2200 |
| 9 | >2200 |
| 10 | >1700 |
| without | 880 |

EXAMPLE 8: Stabilisation of a two-coat metallic stoving lacquer

Recipe for the priming lacquer
  27 parts of polyester resin (L 1850, available from Dynamit Nobel AG),
  3 parts of melamine resin (Maprenal RT, available from Heochst AG),
  2 parts of cellulose acetobutyrate (CAB 531, available from Eastman Chem. Corp.),
  8 parts of aluminium bronze (ALCOA 726, available from the Aluminium Corp. of America),
  10 parts of toluene,
  7 parts of xylene,
  3 parts of butanol,
  25 parts of butyl acetate and
  15 parts of a mixture of aromatic solvents (Solvesso ®150, available from ESSO AG).

Recipe for the finishing lacquer
  58.3 parts of acrylic resin (Viacryl ® VC 373, available from Vianova AG),
  27.3 parts of melamine resin (Maprenal ® MF 590, available from Hoechst AG),
  1.0 part of a 1% solution of a silicone oil in xylene,
  4.0 parts of a mixture of aromatic solvents (Solvesso ®, available from ESSO AG),
  5.4 parts of xylene,
  4.0 parts of ethyl glycol acetate.

The finishing lacquer is stabilised by adding to it 0.6 part of a stabiliser of the invention, corresponding to a concentration of 1% by weight, based on the solids content of the clear lacquer. The pigmented primer lacquer is sprayed to give a coating of 15 μm onto aluminium sheets to which an undercoat of a polyester/epoxy resin lacquer has been applied. After 10 minutes the finishing lacquer is sprayed to give a coating of 30

μm on top of the priming lacquer coating. The samples are exposed to the air for 15 minutes and then stoved for 30 minutes at 120° C.

The coated aluminium sheets are stored for a week under normal climatic conditions (23° C./5% relative humidity) and then exposed to weathering in a QUV device in accordance with ASTM G 53-77. In this text, the samples are moistened for 4 hours at 50° C. and irradiated by UV light for 4 hours in a humid atmosphere at 60° C.

The samples are examined at regular intervals and their appearance is assessed by the TNS crack initiation scale. This scale has 10 degrees of intensity (1–10) and classifies different types of crack formations (A–P) and crack depth (a–f). The weathering time in the exposure device up to a crack formation of 6-8b according to the TNO scale is indicated in Table 2 as crack stability.

TABLE 2

| Stabiliser | Crack stability in hours |
|---|---|
| 1a | >1500 |
| 2 | >1500 |
| 7 | >1500 |
| 9 | >1500 |
| without | 1100 |

What is claimed is:

1. A compound of the formula Ia or Ib

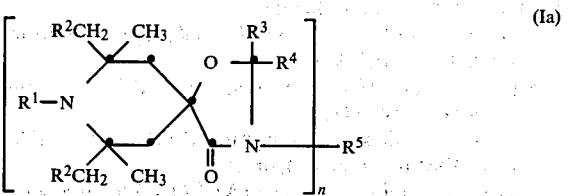

(Ia)

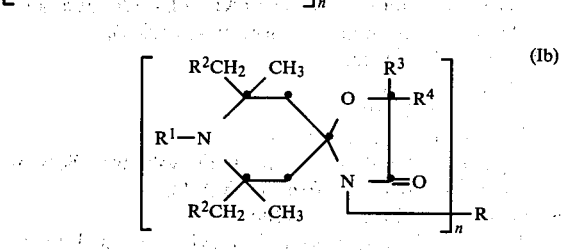

(Ib)

wherein n is 1 or 2;

$R^1$ is $C_2$-$C_{30}$alkanoyl, $C_3$-$C_{20}$alkenoyl, —$CH_2CN$, —CO—N($R^6$)($R^7$), $C_7$-$C_{11}$aroyl, $C_8$-$C_{14}$arylalkanoyl or $C_8$-$C_{20}$alkylaroyl;

$R^2$ is hydrogen or $C_1$-$C_4$alkyl; each of $R^3$ and $R^4$ independently of the other is hydrogen, $C_1$-$C_{30}$alkyl, unsubstituted or chlorine- or alkyl-substituted $C_6$-$C_{10}$aryl, unsubstituted or alkyl-substituted $C_7$-$C_{11}$aralkyl, or $R^3$ and $R^4$, together with the carbon atom to which they are attached, form a cycloalkane or alkylcycloalkane ring containing 5 to 18 carbon atoms, or a group of the formula

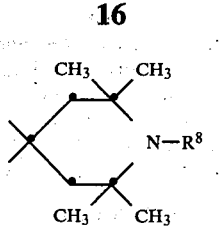

$R^5$, when n is 1, is $C_1$-$C_{30}$alkyl, $C_3$-$C_{20}$alkenyl, unsubstituted or alkyl-substituted $C_7$-$C_{11}$aralkyl, or is $C_5$-$C_{12}$cycloalkyl, $C_2$-$C_{18}$alkanoyl, $C_3$-$C_{18}$alkenoyl, $C_7$-$C_{11}$aroyl, $C_8$-$C_{14}$arylalkanoyl or $C_8$-$C_{20}$alkylaroyl, or $R^5$, when n is 2, is $C_2$-$C_{30}$alkylene, $C_2$-$C_{30}$alkenylene or $C_8$-$C_{18}$arylenedialkylene;

$R^6$ is hydrogen, $C_1$-$C_{18}$alkyl, $C_5$-$C_8$cycloalkyl, $C_7$-$C_{15}$aralkyl or $C_6$-$C_{10}$aryl;

$R^7$ is $C_1$-$C_{18}$alkyl, $C_5$-$C_8$cycloalkyl, $C_7$-$C_{15}$aralkyl or $C_6$-$C_{10}$aryl; or $R^6$ and $R^7$, together with the nitrogen atom, form a pyrrolidine, piperidine, morpholine or piperazine ring; and $R^8$ is hydrogen, $C_1$-$C_{12}$alkyl, $C_3$-$C_5$alkenyl, $C_3$-$C_5$alkynyl, unsubstituted or alkyl-substituted $C_7$-$C_{11}$aralkyl, $C_2$-$C_8$alkanoyl, $C_3$-$C_{18}$alkenoyl, —$CH_2CN$ or —CO—N($R^6$)($R^7$).

2. A compound according to claim 1 of the formula Ia or Ib, wherein $R^1$ is $C_2$-$C_{12}$alkanoyl, $C_3$-$C_5$alkenoyl, phenylacetyl, —$CH_2CN$ or —CO—N($R^6$)($R^7$);

$R^2$ is hydrogen;

each of $R^3$ and $R^4$ independently of the other is hydrogen, $C_1$-$C_{12}$alkyl, $C_7$-$C_{12}$aralkyl or phenyl substituted by $C_1$-$C_4$alkyl, or $R^3$ and $R^4$, together with the carbon atom to which they are attached, form a cycloalkane or alkylcycloalkane ring containing 5 to 12 carbon atoms or a group of the formula

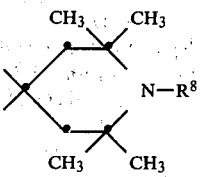

$R^5$, when n is 1, is $C_1$-$C_{18}$alkyl, $C_3$-$C_6$alkenyl, $C_5$-$C_6$cycloalkyl, $C_7$-$C_{12}$aralkyl, $C_2$-$C_{12}$alkanoyl or $C_3$-$C_{12}$alkenoyl, and when n is 2, is $C_2$-$C_{18}$alkylene, $C_4$-$C_{12}$alkenylene or xylylene;

$R^6$ is hydrogen, $C_1$-$C_{12}$alkyl, $C_5$-$C_6$cycloalkyl, $C_7$-$C_{12}$aralkyl or phenyl;

$R^7$ is $C_1$-$C_{12}$alkyl, $C_5$-$C_6$cycloalkyl, $C_7$-$C_{12}$aralkyl or $C_6$-$C_{10}$aryl, or $R^6$ and $R^7$, together with the nitrogen atom to which they are attached, form a pyrrolidine, piperidine, morpholine or piperazine ring; and $R^8$ is hydrogen, $C_1$-$C_6$alkyl, $C_3$-$C_5$alkenyl, benzyl, $C_2$-$C_{12}$alkanoyl, $C_3$-$C_{12}$alkenoyl, propargyl or cyanomethyl.

3. A compound according to claim 1 of the formula Ia, wherein n is 1; $R^1$ is $C_2$-$C_{12}$alkanoyl, $C_3$-$C_5$alkenoyl, —CO—N($R^6$)($R^7$) or —$CH_2CN$; $R^2$ is hydrogen; each of $R^3$ and $R^4$ independently of the other is hydrogen, $C_1$-$C_4$alkyl, benzyl or phenyl, or $R^3$ and $R^4$, together with the carbon atom to which they are attached, form a $C_5$-$C_{12}$cycloalkane ring; $R^5$ is $C_1$-$C_6$alkyl, $C_3$-$C_5$alkenyl, benzyl, $C_2$-$C_{12}$alkanoyl or $C_3$-$C_5$alkenoyl; $R^6$ is hydrogen, $C_1$-$C_6$alkyl, cyclohexyl, benzyl or phenyl; and $R^7$ is $C_1$-$C_6$alkyl, cyclohexyl, benzyl or phenyl; or $R^6$ and $R^7$, together with the nitrogen atom to which they are attached, form a pyrrolidine, piperidine, morpholine or piperazine ring.

* * * * *